(12) United States Patent
Cascone

(10) Patent No.: US 11,427,894 B2
(45) Date of Patent: Aug. 30, 2022

(54) COBALT BASED PLATINUM-CONTAINING NOBLE DENTAL ALLOYS

(71) Applicant: The Argen Corporation, San Diego, CA (US)

(72) Inventor: Paul Cascone, Del Mar, CA (US)

(73) Assignee: The Argen Corporation, San Diego, CA (US)

( * ) Notice: Subject to any disclaimer, the term of this patent is extended or adjusted under 35 U.S.C. 154(b) by 0 days.

(21) Appl. No.: 16/938,209

(22) Filed: Jul. 24, 2020

(65) Prior Publication Data

US 2021/0032729 A1 Feb. 4, 2021

Related U.S. Application Data

(60) Provisional application No. 62/882,127, filed on Aug. 2, 2019.

(51) Int. Cl.
*C22C 30/00* (2006.01)
*A61K 6/844* (2020.01)
*A61K 6/80* (2020.01)

(52) U.S. Cl.
CPC .............. *C22C 30/00* (2013.01); *A61K 6/80* (2020.01); *A61K 6/844* (2020.01)

(58) Field of Classification Search
None
See application file for complete search history.

(56) References Cited

U.S. PATENT DOCUMENTS

| | | | |
|---|---|---|---|
| 2,226,079 A | 12/1940 | Spanner | |
| 2,890,114 A | 6/1959 | Ruthardt et al. | |
| 2,946,679 A | 7/1960 | Darling | |
| 3,134,671 A | 5/1964 | Prosen | |
| 3,141,765 A | 7/1964 | Brown et al. | |
| 3,155,467 A | 11/1964 | Yamamoto et al. | |
| 3,764,493 A | 10/1973 | Nicks | |

(Continued)

FOREIGN PATENT DOCUMENTS

| | | |
|---|---|---|
| DE | 1104195 B | 4/1961 |
| DE | 10136997 A1 | 2/2003 |

(Continued)

OTHER PUBLICATIONS

Machine translation of Spohn et al. (WO 2003011231 A1, WO 03/011231 A1). Translated by Google patents May 13, 2021. (Year: 2003).*

(Continued)

*Primary Examiner* — Elizabeth Collister
(74) *Attorney, Agent, or Firm* — KPPB LLP

(57) ABSTRACT

A family of cobalt based dental alloys suitable for PFM and SLM applications that do not exhibit ferromagnetism and that are capable of meeting the ADA requirements for a "noble" alloy are provided. The dental alloys comprise at least 25 wt. % of noble metals selected from either platinum alone or a combination of platinum and ruthenium, and from 23 to 32 wt. % chromium. Additional additive materials may be included in concentrations up to 3 wt. %. The ruthenium optionally comprises up to 8 wt. %, and in some embodiments from at least 5 wt. % to 8 wt. % of the noble metals such that the dental alloys are capable of meeting the ADA requirements for a "noble" alloy.

18 Claims, 2 Drawing Sheets

(56) References Cited

U.S. PATENT DOCUMENTS

| | | | |
|---|---|---|---|
| 3,928,913 | A | 12/1975 | Schaffer |
| 4,038,074 | A | 7/1977 | Davitz |
| 4,098,605 | A | 7/1978 | Nepela et al. |
| 4,123,262 | A | 10/1978 | Cascone |
| 4,179,286 | A | 12/1979 | Knosp |
| 4,195,988 | A | 4/1980 | Ito |
| 4,201,577 | A | 5/1980 | Agarwall et al. |
| 4,253,869 | A | 3/1981 | Prosen |
| 4,255,190 | A | 3/1981 | Prosen |
| 4,350,526 | A | 9/1982 | Schaffer |
| 4,382,709 | A | 5/1983 | Brown |
| 4,382,909 | A | 5/1983 | Zwingmann |
| 4,387,072 | A | 6/1983 | Schaffer |
| 4,459,263 | A * | 7/1984 | Prasad ............ C22C 19/07 420/437 |
| 4,539,176 | A | 9/1985 | Cascone |
| 4,569,825 | A | 2/1986 | Dvivedi et al. |
| 4,591,483 | A | 5/1986 | Nawaz |
| 4,681,735 | A | 7/1987 | Groll et al. |
| 4,735,772 | A | 4/1988 | van der Zel |
| 4,917,861 | A | 4/1990 | Schaffer et al. |
| 5,174,954 | A | 12/1992 | Schaffer et al. |
| 5,236,789 | A | 8/1993 | Cowie et al. |
| 5,423,680 | A | 6/1995 | Prasad |
| 5,529,642 | A | 6/1996 | Sugahara et al. |
| 5,560,742 | A | 10/1996 | Groll et al. |
| 5,799,386 | A | 9/1998 | Ingersoll et al. |
| 5,916,518 | A | 6/1999 | Chesnes |
| 6,103,383 | A | 8/2000 | Prasad |
| 6,290,501 | B1 | 9/2001 | Grau et al. |
| 6,365,285 | B1 | 2/2002 | Chesnes |
| 6,554,920 | B1 | 4/2003 | Jackson et al. |
| 6,613,275 | B1 | 9/2003 | Vuilleme |
| 6,656,420 | B2 | 12/2003 | Prasad et al. |
| 6,756,012 | B2 | 6/2004 | Prasad |
| 6,994,549 | B2 | 2/2006 | Brodkin et al. |
| 7,084,370 | B2 | 8/2006 | Hagemeister et al. |
| 7,569,116 | B2 | 8/2009 | Ono et al. |
| 7,794,652 | B2 | 9/2010 | Cascone |
| 8,623,272 | B2 | 1/2014 | Prasad et al. |
| 2002/0041820 | A1 | 4/2002 | Prasad |
| 2002/0122741 | A1 | 9/2002 | Prasad et al. |
| 2005/0158693 | A1 | 7/2005 | Prasad et al. |
| 2006/0147334 | A1* | 7/2006 | Cascone ............ C22C 30/00 420/35 |
| 2008/0070058 | A1 | 3/2008 | Dasgupta et al. |
| 2008/0070192 | A1 | 3/2008 | Dasgupta et al. |
| 2008/0085828 | A1 | 4/2008 | Khan et al. |
| 2008/0232998 | A1* | 9/2008 | Prasad ............ C22C 1/06 420/436 |
| 2010/0266443 | A1 | 10/2010 | Cascone |
| 2011/0275033 | A1 | 11/2011 | Dasgupta et al. |
| 2012/0244035 | A1 | 9/2012 | Cascone et al. |
| 2014/0170598 | A1* | 6/2014 | Abend ............ C22C 1/0466 433/208 |

FOREIGN PATENT DOCUMENTS

| | | | |
|---|---|---|---|
| EP | 0036556 A1 | 9/1981 | |
| EP | 0347614 A1 | 12/1989 | |
| EP | 1595523 A1 | 11/2005 | |
| EP | 1900836 A1 | 3/2008 | |
| FR | 2015889 A | 4/1970 | |
| FR | 2733416 A1 | 10/1996 | |
| FR | 2750858 A1 | 1/1998 | |
| FR | 2750867 A1 | 1/1998 | |
| GB | 2421513 | 6/2006 | |
| JP | 52128823 | 10/1977 | |
| WO | WO-03011231 A1 * | 2/2003 | ............ A61K 6/884 |
| WO | 2007042841 A1 | 4/2007 | |
| WO | 2008115879 A1 | 9/2008 | |
| WO | 2009046260 A1 | 4/2009 | |
| WO | 2010/123488 A1 | 10/2010 | |
| WO | 2010123488 A1 | 10/2010 | |

OTHER PUBLICATIONS

International Preliminary Report on Patentability for International Application No. PCT/US2008/078686, Report dated Dec. 23, 2014, 6 Pgs.

European Search Report, dated Nov. 20, 2002, for Application No. PCT/EP02/08246.

European Search Report, dated Sep. 5, 2006, for Application No. GB0526021.1, 2pgs.

International Preliminary Report on Patentability for International Application No. PCT/US2008/057253, Report dated Sep. 22, 2009, 6 Pgs.

International Preliminary Report on Patentability for International Application No. PCT/US2009/041096, Report dated Oct. 25, 2011, Mailed Nov. 3, 2011, 5 Pgs.

International Search Report for International Application No. PCT/US 09/41096, date completed May 26, 2009, dated Jun. 12, 2009, 2 pgs.

International Search Report for International Application No. PCT/US2008/078686, filed Oct. 3, 2008, Report completed Nov. 24, 2008, dated Dec. 12, 2008, 2 pgs.

International Search Report for International Application PCT/US2008/057253, filed Mar. 17, 2008, Report completed May 30, 2008, dated Jul. 31, 2008, 2 pgs.

Written Opinion for International Application No. PCT/US2008/078686, filed Oct. 3, 2008, Opinion completed Nov. 25, 2008, dated Dec. 12, 2008, 5 pgs.

Written Opinion for International Application PCT/US2008/057253, filed Mar. 17, 2008, Report completed May 30, 2008, dated Jul. 31, 2008, 5 pgs.

Written Opinion of the International Searching Authority for International Application No. PCT/US 09/41096, date completed May 26, 2009, dated Jun. 12, 2009, 4 pgs.

International Preliminary Report on Patentability for International Application No. PCT/US2008/078686, Report dated Dec. 23, 2014, 6 Pgs. Apr. 7, 2010.

Kinouchi et al., "Pd-Co Dental Casting Ferromagnetic Alloys", J Dent Res, Jan. 1981, vol. 60, No. 1, pp. 50-58.

* cited by examiner

COBALT BASED PLATINUM-CONTAINING NOBLE DENTAL ALLOYS

CROSS-REFERENCE TO RELATED APPLICATIONS

The current application claims the benefit of and priority under 35 U.S.C. § 119 (e) to U.S. Provisional Patent Application No. 62/882,127 entitled "Cobalt Based Platinum-Containing Noble Dental Alloys" filed Aug. 2, 2019. The disclosure of U.S. Provisional Patent Application No. 62/882,127 is hereby incorporated by reference in its entirety for all purposes.

FIELD OF THE INVENTION

The current application is directed to a cobalt based noble dental alloy, and more specifically to a cobalt based noble dental alloy containing platinum where the alloy composition ensures a dental alloy material that does not exhibit ferromagnetic behavior.

BACKGROUND OF THE INVENTION

Dental alloys employed in porcelain-fused-to-metal (PFM) processing or selective laser melting (SLM) processing may be classified into several groups, including gold based, palladium based, cobalt based, and titanium based. In addition to their functional properties, e.g., ductility, thermal expansion, and non-magnetism, one of the most important criteria in deciding which metals to use is cost, in particular the cost of the precious metal. The cost of the alloy is dependent upon the commodity prices of the alloy components. For alloys containing precious metals, such as, for example, gold, silver, palladium, etc., traditionally, palladium has been preferred for its lower cost per ounce. However, palladium has become increasingly important in industrial applications resulting in increased commodity prices for the metal.

While the economic advantage of replacing palladium as the precious metal component of the alloy is obvious, the functional characteristics of other precious metal containing alloys do not compare with those containing gold or palladium, and for this reason they are not generally used in dental products. For example, in general, metal alloys containing platinum have thermal expansion properties that are not as suitable for the traditional dental porcelains used in the porcelain fused to metal fabrication technique.

Accordingly, while a number of different "noble" dental alloys containing precious metals have been achieved through the incorporation of gold and/or the platinum group metals, to date no successful commercial formulation of a cobalt based high platinum content alloy has been obtained that is non-magnetic and consistent with the American Dental Association (ADA) guidelines for "noble" alloys required for use in dental products (i.e. alloys having at least 25% gold or platinum group elements).

SUMMARY OF THE INVENTION

The invention is directed to improved cobalt based platinum containing alloys, and in some embodiments to improved cobalt based platinum containing alloys that do not exhibit ferromagnetic properties and have improved thermal expansion properties.

Many embodiments are directed to non-magnetic cobalt based dental alloys including:
40 wt. % to 50 wt. % Co;
19 to 27 wt. % Pt;
up to 8 wt. % Ru; and
23 wt. % to 32 wt. % Cr;
wherein the Pt comprises or combination of Pt and Ru comprise from 25 wt. % to 35 wt. % of the dental alloy composition; and
wherein the alloy is non-magnetic and has a coefficient of thermal expansion between 13.9 to $15.2 \times 10^{-6}$ $K^{-1}$ at 500° C.

In still many embodiments, the alloy further comprises up to about 3 wt. % of at least one additive material selected from the group consisting of molybdenum, manganese, aluminum, boron, cerium, gallium, germanium and silicon.

In yet many embodiments, the alloy comprises from about 5 to 8 wt. % ruthenium.

In still yet many embodiments, the alloy further comprises less than 5 wt. % of at least one trace additive selected from the group consisting of copper, nickel and iron.

In yet still many embodiments, the sum of Pt and Ru is about 25 wt. %.

In still yet many embodiments, the alloy composition comprises 45.0 wt. % cobalt, 29.3 wt. % chromium, 20 wt. % platinum, and 5.7 wt. % ruthenium.

In yet still many embodiments, the alloy has a thermal expansion coefficient of from 14.3 to $14.7 \times 10^{-6}$ $K^{-1}$ at 500° C.

In yet still many embodiments, the alloy has a thermal expansion coefficient of from 14.6 to $15 \times 10^{-6}$ $K^{-1}$ at 600° C.

In still yet many embodiments, the alloy has a liquidus temperature of from 1370 to 1420° C.

In yet still many embodiments, the alloy has a Vickers Hardness of from 180 to 332 HV, a tensile strength of from 900 to 1200 MPa, a Young's modulus of from 470 to 780 MPa, and an elongation of from 2 to 14%.

Various embodiments are directed to a dental product including:
a body for dental application, said body being formed of a non-magnetic cobalt based dental alloy including:
40 wt. % to 50 wt. % Co;
19 wt. % to 27 wt. % Pt;
up to 8 wt. % Ru; and
23 wt. % to 32 wt. % Cr;
wherein the Pt comprises or combination of Pt and Ru comprise from 25 wt. % to 35 wt. % of the dental alloy composition; and
wherein the alloy is non-magnetic and has a coefficient of thermal expansion between 13.9 to $15.2 \times 10^{-6}$ $K^{-1}$ at 500° C.

In still various embodiments, the alloy further comprises up to about 3 wt. % of at least one additive material selected from the group consisting of molybdenum, manganese, aluminum, boron, cerium, gallium, germanium and silicon.

In yet various embodiments, the alloy comprises from 5 to 8 wt. % ruthenium.

In still yet various embodiments, the alloy further comprises less than 5 wt. % of at least one trace additive selected from the group consisting of copper, nickel and iron.

In yet still various embodiments, the sum of Pt and Ru is about 25 wt. %.

In still yet various embodiments, the alloy composition comprises 45.0 wt. % cobalt, 29.3 wt. % chromium, 20 wt. % platinum, and 5.7 wt. % ruthenium.

In yet still various embodiments, the alloy has a thermal expansion coefficient of from about 14.3 to $14.7 \times 10^{-6}$ $K^{-1}$ at 500° C.

In yet still various embodiments, the alloy has a thermal expansion coefficient of from about 14.6 to $15 \times 10^{-6}$ $K^{-1}$ at 600° C.

In still yet various embodiments, the alloy has a liquidus temperature of from 1370 to 1420° C.

In yet still various embodiments, the alloy has a Vickers Hardness of from 180 to 332 HV, a tensile strength of from 900 to 1200 MPa, a Young's modulus of from 470 to 780 MPa, and an elongation of from 2 to 14%.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein.

DETAILED DISCLOSURE

Figure 1A:
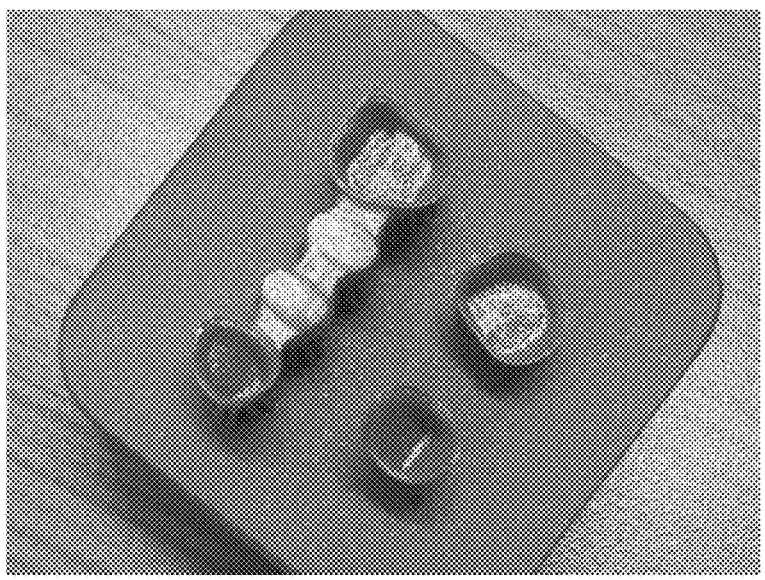
FIGS. 1a to 1d provide images of dental appliances formed from exemplary alloy compositions in accordance with embodiments.

The embodiments of the invention described herein are not intended to be exhaustive or to limit the invention to precise forms disclosed. Rather, the embodiments selected for description have been chosen to enable one skilled in the art to practice the invention. It will be understood that herein, the term "non-magnetic", where used, refers to materials that do not demonstrate ferromagnetic properties.

Embodiments are directed to a family of cobalt based dental alloys suitable for PFM and SLM applications that do not exhibit ferromagnetism and that are capable of meeting the ADA requirements for a "noble" alloy. In various such embodiments, the dental alloys comprise cobalt, at least 23 wt. % and up to 32 wt. % chromium, and from 25 wt. % to 35 wt. % of noble metals, either platinum alone or a combination of platinum and ruthenium. In many embodiments, the platinum comprises from 19 wt. % to 27 wt. %, and the ruthenium comprises up to 8 wt. %, and in some embodiments at least 5 wt. % but no more than 8 wt. % of the overall noble metals such that the dental alloys are capable of meeting the ADA requirements for a "noble" alloy. Some embodiments may also include additional additive materials in amount of up to 3 wt. %.

Alloys for use in dental applications, such as forming metal/porcelain composites, require a very delicate balancing of a number of properties. These properties include, among other things:

Aesthetics: The alloy/porcelain composite needs to reproduce the normal coloration of natural dentition.

Mechanical Properties: International Organization for Standardization (ISO) standard ISO22674 sets yield strength (from about 80 to 500 MPa), elongation after fracture (from 2 to 18%) and Young's modulus (from 150 GPa) values for dental alloys for different dental applications, from low stress bearing single-tooth fixed restorations to appliances that require a combination of high stiffness and strength, e.g., thin removable partial dentures.

Physical Properties: Although the above-mentioned standards do not require either minimum or maximum values for the coefficient of thermal expansion (CTE), the CTE value is important particularly for PFM techniques to ensure compatibility between the porcelain and metal materials.

Magnetic Properties: It is desirable that all alloys for dental applications be nonmagnetic, i.e., not demonstrate ferromagnetic properties. Specifically, alloys that react to a magnetic field are not desirable in dental applications because they can interfere with medical imaging. Dental implants that are ferromagnetic may interfere with medical imaging procedures such as MRI. Different types of MRI are characterized based on the magnetic field strength: low-field MRI scanners (0.23 T to 0.3 T), high-field MRI scanners (1.5 T to 3.0 T), and ultra-high field MRI scanners (7.0 T to 10 T). MRI is considered contraindicated in patients with ferromagnetic metallic implants or other ferromagnetic materials, primarily because of the potential risks associated with movement or dislodgment of these objects under the magnetic field. Artifacts caused by metallic objects, such as dental crowns, dental implants and metallic orthodontic appliances, are a common problem in head and neck MRI.

Many cobalt-based alloys capable of being used in dental applications have been proposed. Most of these alloys combine chromium and cobalt along with sufficient noble metals to qualify under the ADA requirements as a "noble" alloy, e.g., having at least 25 wt. % of some combination of noble metals, such as, for example, gold, palladium, ruthenium, etc. TABLE 1, below provides a selection of these alloys for comparison.

TABLE 1

Conventional Co—Cr Dental Alloys

| Lead Inventor | Patent/ Publication No. | Composition (wt. %) |
| --- | --- | --- |
| Prasad | U.S. Pat. No. 8,623,272 | 15-30% Cr, 25% Pd, balance Co |
| Wieland | WO2003011231 | 1-35% Cr, 12-18% Pt, 7-13% Ru, 40-70% Co |
| Cascone | U.S. Pat. No. 7,794,652 | 15-30% Cr, >25% noble metal (at least 15% Ru), balance Fe, Ni & Co |
| Obrowski | DE1104195 | 20-40% Cr, 20-50% Ru, 29-45% Co |
| Bego | US 2014/0170598 | 25-30% noble metals, 22-28% Cr, 6-10% Mo/W, 36-47% Co |
| Dasgupta | US 2011/0275033 | 20-90% Pd, 10-80% Co |

In each case, the balance of elements in the alloy is carefully selected to provide some improvement in the functional characteristics of the base metal alloy. However, as demonstrated above so far these efforts have focused on either palladium containing alloys, or in the case of the Wieland patent, alloys with mixtures of platinum and other noble metals along with high concentrations of ruthenium (e.g., up to 13% with a preference of at least 10%). This is understandable as historically palladium and ruthenium have generally been the most cost effective of the noble metals. However, with the rise in demand, the cost of palladium has increased significantly. In addition, while Prasad and Dasgupta state the palladium containing alloys are nonmagnetic, Bego describes the cobalt based dental alloys are paramagnetic. None of Wieland, Cascone or Obrowski discusses about magnetism in the alloys. Embodiments herein disclosed expand the effort to improve the base metal-based alloys through the use of platinum in combination with judicious concentrations of ruthenium, to form non-magnetic chromium cobalt-platinum alloys formulated to meet the requirements for use in dental alloys.

In various embodiments, non-magnetic dental alloys have the following general composition:
23 to 32 wt. % chromium;
19 wt. % to 27 wt. % platinum;
up to 8 wt. % ruthenium; and
40 wt. % to 50 wt. % cobalt;
wherein the Pt comprises or combination of Pt and Ru comprise from 25 wt. % to 35 wt. % of the dental alloy composition.

Although not specified in the above formulation of the alloy, it should be understood that in many embodiments the alloy contains a minimum concentration of cobalt of about 40 wt. %, and in many other embodiments up to 50 wt. %. The alloy may also include other additives to improve specific properties, such as the casting or grain refinement properties. These additional materials may include molybdenum, manganese, gallium, silicon, boron, germanium, aluminum and cerium in concentrations of up to 3.0 wt. % in several embodiments.

In many embodiments, ruthenium can be added to the alloy and adjust the thermal expansion properties to be more suitable for dental implants. The addition of ruthenium to the alloy can lower the thermal expansion of the alloy and make it compatible with more PFM materials. In various embodiments, the concentration of ruthenium is up to 8 wt. %. Some embodiments include that when ruthenium concentration exceeds 8 wt. %, the alloy starts to show ferromagnetism. In a number of embodiments, the concentration of ruthenium is lower than 8 wt. % to ensure the alloy is nonmagnetic.

Exemplary compositions for dental alloys according to embodiments comprise: platinum from 19 to 27 wt. %, ruthenium 8 wt. %, chromium from 23 to 32 wt. %, cobalt from 40 to 50 wt. %, and additives, including, for example, molybdenum, manganese and silicon in amounts up to ~3%. TABLE 2, below, provides the composition of a set of exemplary alloys according to embodiments providing compositional limits and the effects of changes to those compositional limits on the properties, including the magnetic properties, of those alloys.

Alloys according to these embodiments meet all the criteria for use as dental materials and for use in PFM and SLM techniques including:
Not exhibiting ferromagnetic behavior;
Having sufficient ductility for selective laser melting;
Meeting requirements for ISO 22674 (as set forth in Table 4, below); and
Having a thermal expansion between 13.9 and 15.2×10$^{-6}$ K$^{-1}$ at 500° C.

Specifically, as demonstrated in TABLE 2, within the 25 wt. % noble metal requirements for meeting the ADA "noble" alloy requirement, a platinum content of from 19 wt. % to 27 wt. %, and platinum's general enabling effect, can in some embodiments reduce the need for large additions of other materials such as chromium, molybdenum, tungsten, etc. Many embodiments require that the alloy material formed is non-magnetic. Many embodiments include that alloying cobalt with platinum and chromium within the disclosed weight percentages, renders these alloys nonmagnetic. However, the coefficient of thermal expansion for these alloys can be unsuitable for use in some dental applications. With the addition of a carefully titrated amount of ruthenium, i.e., greater than 5 wt. % but less than 8 wt. % the CTE of these alloys can be made compatible with dental applications without resulting in the alloys exhibiting ferromagnetic properties in accordance to many embodiments. In several embodiments, the concentration of ruthenium is maintained up to 8 wt. % to ensure the alloy is nonmagnetic. In some embodiments, ruthenium content in an alloy is higher than 5 wt. % to achieve compatible CTE in some dental implants. As shown in TABLE 2, when an alloy has a content of ruthenium of less than 5 wt. % the CTE of the alloys is not suitable for some dental applications, and where the concentration of ruthenium increases to 8 wt. % or more the alloys demonstrate ferromagnetic properties, but where the alloy falls within this range it possesses both excellent CTE and non-magnetic properties in accordance to several embodiments. Accordingly, various embodiments may comprise a trinary cobalt/chromium/platinum composition, and in some embodiments a concentration of up to 8 wt. % ruthenium may be added to improve the physical and thermal properties of the alloys. A summary of various embodiments of dental alloys against alloys lying outside the proposed compositional range is provided in TABLE 2, below.

TABLE 2

Comparison of Dental Alloy Compositions

| Component | Alloy 1 | Alloy 10 | Alloy 6 | Alloy 7 | Alloy 11 |
|---|---|---|---|---|---|
| Pt (wt. %) | 25.0 | 20.0 | 20.0 | 15.0 | 25.0 |
| Ru (wt. %) | — | 5.7 | 5.7 | 11.4 | — |
| Cr (wt. %) | 30.0 | 29.3 | 25.0 | 25.0 | 30.0 |
| Mo (wt. %) | — | — | — | — | 3.0 |
| Co (wt. %) | 45.0 | 45.0 | 49.3 | 48.6 | 42.0 |
| Magnetic Properties | Non-mag | Non-mag | Non-mag | Magnetic | Non-mag |
| CTE at 500° C. (×10$^{-6}$ K$^{-1}$) | 14.7 | 14.3 | 14.6 | — | 14.7 |
| CTE at 600° C. (×10$^{-6}$ K$^{-1}$) | 15 | 14.6 | 14.9 | — | 15 |
| Vickers Hardness (HV) | 180 | 315 | 332 | — | 266 |

One exemplary composition of an alloy according to embodiments is provided in TABLE 3, below. This table also provides an exemplary composition for a conventional palladium-containing alloy sold under the tradename Noble-Crown NF® for comparison.

TABLE 3

Compositional Comparison

| Element | NobleCrown NF ® (wt. %) | Exemplary Compositions (wt. %) |
|---|---|---|
| Pd | 25 | 0 |
| Pt | 0 | 20 |
| Ru | 0 | 5.7 |
| Cr | 20 | 29.3 |
| Mo | 10 | 0 |
| Co | 45 | 43.5 |
| Mn, Si | — | <1 |

The physical and thermal properties in accordance to some embodiments of the exemplary compositions listed in TABLE 3 compared against the prior art palladium alloy are provided in TABLE 4 and TABLE 5, below.

TABLE 4

Exemplary Physical Properties

| Property | NobleCrown NF ® | Exemplary Compositions |
|---|---|---|
| Vickers Hardness | 335 HV | 180-332 HV |
| Tensile Strength | 690 MPa | 900 to 1200 MPa |
| Yield Strength | 620 MPa | 470 to 780 MPa |
| Elongation | 4% | 2 to 14% |

Alloys formed in accordance with embodiments of the present invention exhibit non-magnetic properties. In many embodiments, the non-magnetic chromium cobalt-platinum alloys also exhibit a wide variety of other physical properties that make them particularly promising for use in dental applications, and comparable or superior to conventional palladium-based alloys. Exemplary physical properties of alloys in accordance to some embodiments are listed in TABLE 4. In many embodiments, the exemplary composition alloys show Vickers Hardness of from 180 to 330 HV, tensile strengths of from 900 to 1200 MPa, yield strengths of from 470 to 780 MPa, and elongation fracture parameters of from 2 to 14%. In some embodiments, the alloy exhibits Vickers Hardness of about 314 HV, tensile strength of about 1000 MPa, yield strength of about 713 MPa, and elongation fracture parameter of about 10%.

In many embodiments, the exemplary composition alloys show promising thermal properties, including liquidus temperatures below about 1500° C. (typically below 1450° C.), which makes them adaptable for use with all standard casting, molding and shaping processes, as well as with new non-casting procedures. In addition, the exemplary alloy compositions in accordance to many embodiments can be ground using traditional dental laboratory grinding media, making the alloy suitable for use with newer CAD/CAM and powder metallurgical applications where no casting is required. Substrates or final restorations can be milled from blocks made from these alloys. As powders, these alloys can be used either to create three dimensional performs utilizing appropriate binders and then be sintered or directly be sintered/melted such as for example, with a laser, to create substrate or final restoratives in various embodiments. Exemplary disclosures of such processes can be found, for example, in U.S. Pat. Nos. 7,084,370 and 6,994,549, the disclosures of which are incorporated herein by reference. It should be understood that while some prior art laser sintering techniques specify a specific range of useable alloy particulate sizes, the alloys in many embodiments are contemplated for use in laser sintering techniques over all possible particulate size ranges.

In addition to the improved castability of these materials, the alloys show a wide variety of thermal expansion coefficients, namely from about $13.9 \times 10^{-6}$ to about $15.2 \times 10^{-6}$ $K^{-1}$ (as measured from about 25 to 500° C.) in accordance to several embodiments. Some embodiments include that the alloys can be used with all standard porcelains on the marketplace due to their wide range of thermal expansion coefficients. Examples of compatible porcelains with non-magnetic cobalt based dental alloys include (but are not limited to): high fusing conventional porcelains that have thermal expansion coefficients from about 13 to $15 \times 10^{-6}$ $K^{-1}$, and low fusing porcelains that have thermal expansion coefficients from about 15 to $16 \times 10^{-6}$ $K^{-1}$. Exemplary values for CTE and melting temperature ranges of exemplary compositions alloys in accordance to some embodiments are provided in TABLE 5, below, and are also comparable with conventional palladium-based alloys. In many embodiments, the exemplary alloy has CTE at 500° C. from about 14.3 to $14.7 \times 10^{-6}$ $K^{-1}$, and CTE at 600° C. from about 14.6 to $15 \times 10^{-6} K^{-1}$. In several embodiments, the exemplary alloy has CTE at 500° C. about $14.3 \times 10^{-6} K^{-1}$, and CTE at 600° C. about $14.6 \times 10^{-6} K^{-1}$. In some embodiments, the exemplary composition alloys have a melting range from about 1370 to about 1420° C.

TABLE 5

Exemplary Thermal Properties

| Property | NobleCrown NF ® | Exemplary Compositions |
|---|---|---|
| CTE at 500° C. | $14.4 \times 10^{-6} K^{-1}$ | 14.3-14.7 ($\times 10^{-6} K^{-1}$) |
| CTE at 600° C. | $14.8 \times 10^{-6} K^{-1}$ | 14.6-15 ($\times 10^{-6} K^{-1}$) |
| Melting Range | 1250-1290° C. | 1370-1420° C. |

Non-magnetic chromium cobalt-platinum alloys according to embodiments have been tested for compliance with both the ISO 9693-1 requirement and the rigorous ISO 22674 Type 4 requirement for appliances with thin sections that are subject to very high forces: for example, removable partial dentures, clasps, thin veneered crowns, wide-span bridges or bridges with small cross-sections, bars, attachments, and implant retained superstructures. These requirements and the results of tests with an exemplary platinum-containing alloy according to embodiments is provided in TABLE 6, below.

TABLE 6

Results of ISO Testing of Exemplary Alloys

| Test | Requirement | Exemplary Alloy Results |
|---|---|---|
| ISO 22674 (2006) | | |
| Classification | Type 4 | |
| Chemical composition | — | 43.5 Co, 29.3 Cr, 20 Pt, 5.7 Ru (wt. %) |
| ADA Classification | Minimum 25 wt. % (Pt + Ru) | Noble |
| Hazardous elements | Be, Cd < 0.02 wt. % | none |
| Biocompatibility | Direct cytotoxicity | Passed |
| Young's Modulus | — | 190 MPa |
| Tensile Strength | — | 1000 MPa |
| Proof Strength | 325 MPa | 713 MPa |
| Elongation | 2% | 10% |
| Density | — | 9.45 g/cc |
| Corrosion Resistance | <200 µg/cm² | <10 µg/cm² |
| Solidus Temperature | — | 1370° C. |
| Liquidus Temperature | — | 1420° C. |
| Thermal Expansion Coefficient | — | $14.3 \times 10^{-6} K^{-1}$ at 500° C. $14.6 \times 10^{-6} K^{-1}$ at 600° C. |
| ISO 9693-1 (2012) | | |
| metal-ceramic de-bonding/crack-initiation strength | 25 MPa minimum | 45 MPa |

In addition to the main components, many embodiments include alloys that may contain concentrations of other additives to improve specific properties. In some embodiments, small concentrations (up to about 3 wt. %) of molybdenum, manganese, gallium, silicon, boron, aluminum, germanium and cerium can serve to deoxidize, lower the melting range, and improve the castability of the alloys.

In certain embodiments, the addition of gallium can lower the melting range of the alloy so that the material can be cast with a gas-oxygen torch. In a number of embodiments, small silicon and boron additions can also be used to improve the alloy's thermal expansion and castability. Many embodiments also include that these additives may not be essential. For example, if the alloy is to be cast by induction heating, then the melting range can be higher eliminating the need for any of these additives in accordance with some embodiments. Regardless, based on its castability and non-magnetic properties, one particularly preferred non-magnetic alloy in accordance with some embodiments is formed having the following composition: cobalt 45.0 wt. %, chromium 29.3 wt. %, platinum 20 wt. %, and ruthenium 5.7 wt. %.

It is appreciated that the above compositions are not exclusive. Those of skill in the art will be aware that some of the materials can be substituted or additional materials may be added without altering the key properties of the alloys of the current invention. For example, it is well known that small amounts of cobalt and platinum can be substituted with copper, nickel and iron. Alternatively, small concentrations (less than 5 wt. %) of these materials may also be added or be found in the alloy as impurities without affecting the properties of the overall composition.

Figure 1B:
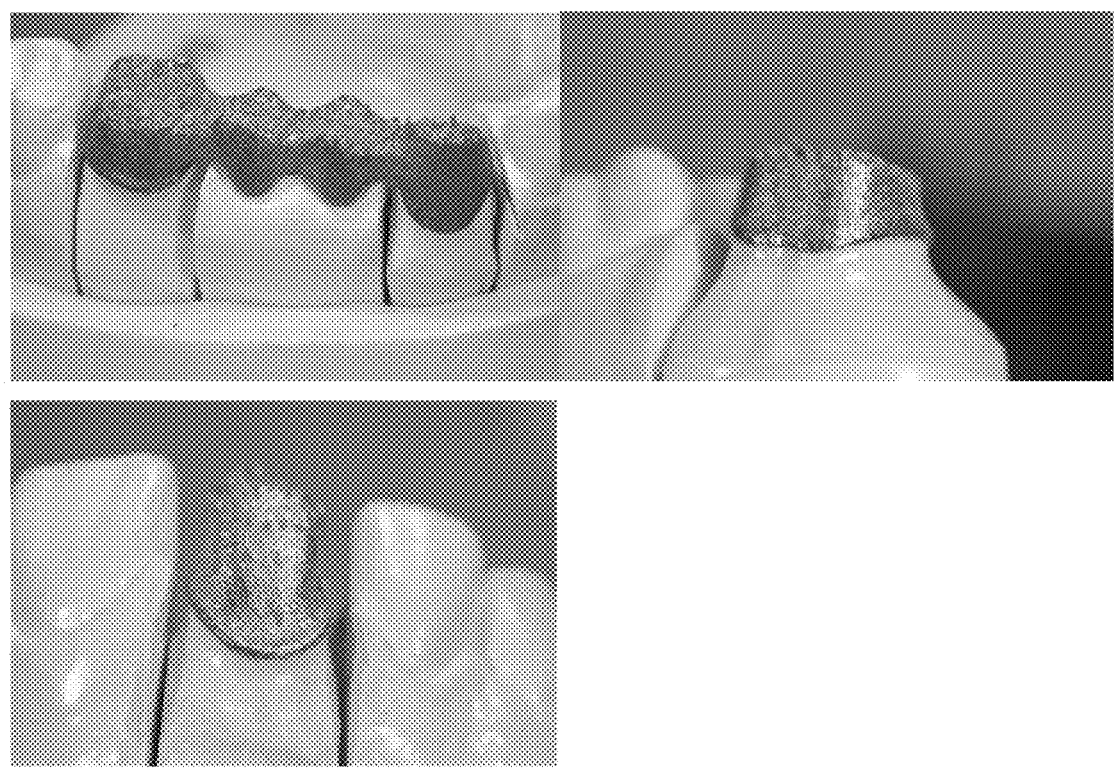
Figure 1C:
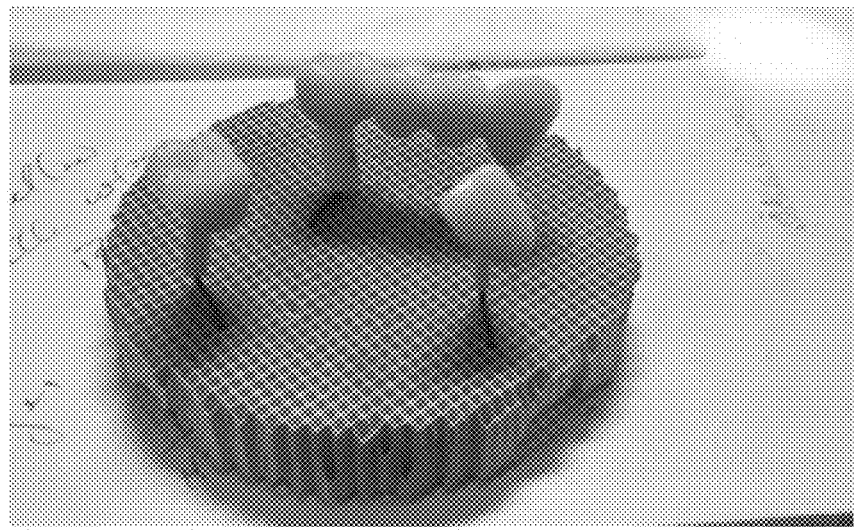
Figure 1D:
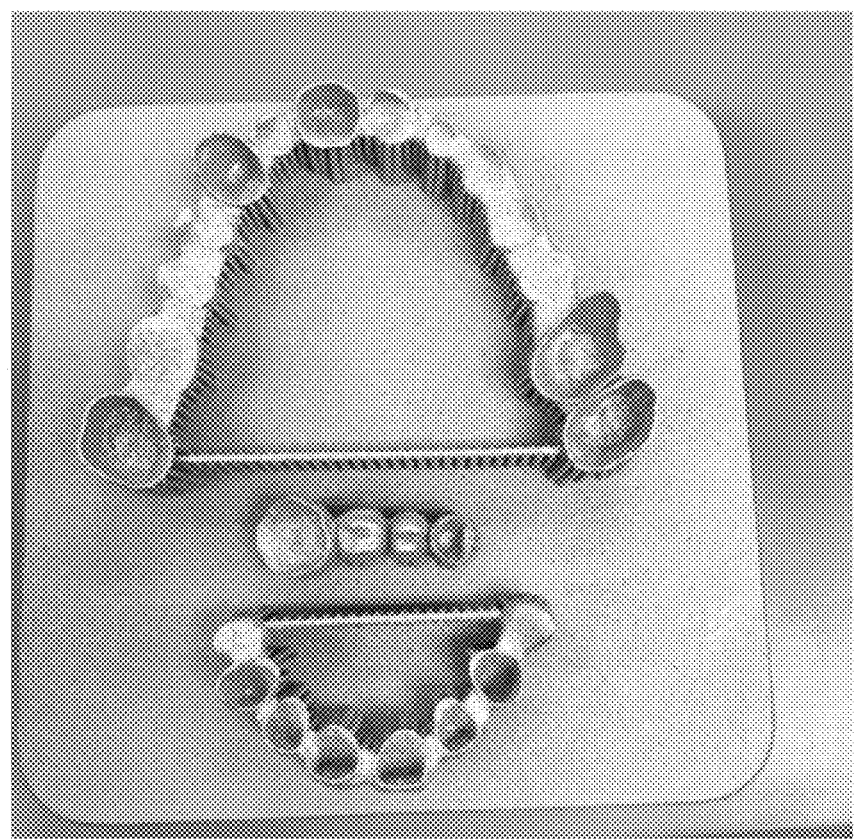

In several embodiments, exemplar compositions are successfully bonded to several popular dental porcelains to demonstrate the utility of these alloys for dental products. In some embodiments, the utility of the materials for dental applications have been tested by fabricating both single crowns and bridgework. In various embodiments, the alloys can be processed using standard foundry processing techniques for cobalt alloys, indicating that the alloys can be useable with typical mass production casting and/or molding techniques. Examples of fabricated crowns and bridgework using non-magnetic cobalt based dental alloys in accordance with some embodiments of the invention are shown in FIGS. 1a to 1d. FIG. 1a illustrates dental crowns made of non-magnetic cobalt based dental alloys are compatible with SLM techniques. FIG. 1b shows dental crowns made of non-magnetic cobalt based dental alloys fit good. FIG. 1c illustrates dental crowns made of non-magnetic cobalt based dental alloys with Ceramco porcelain. FIG. 1d shows bridgework made of non-magnetic cobalt based dental alloys are compatible with SLM techniques.

In some embodiments, biological testing has been completed on ruthenium containing alloys and has determined alloys of this type to be non-cytotoxic. Similar cytotoxicity tests have been completed for the cobalt based dental alloys with similar results in accordance with certain embodiments.

Although the above description has focused on a range of compositions for the alloys in many embodiments, several embodiments are directed to a method of manufacturing a dental product generally comprising the steps of providing an alloy having a composition in accordance with the above described embodiments and then shaping that alloy using any suitable means. As discussed above, the alloys in several embodiments allow for the use of a number of conventional shaping techniques, such as, casting and molding. Moreover, in various embodiments the alloys may allow for the use of more recent advances in shaping technologies, such as, for example, selective laser sintering. It should be understood that any of these techniques or a combination thereof may be used with the alloys in accordance to embodiments.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A cobalt based dental alloy comprising:
   40 wt. % to 50 wt. % Co;
   19 wt. % to 27 wt. % Pt;
   up to 6 wt. % Ru; and
   23 wt. % to 32 wt. % Cr;
   wherein the Pt comprises or combination of Pt and Ru comprise from 25 wt. % to 33 wt. % of the dental alloy composition;
   wherein the alloy has a liquidus temperature of from 1370 to 1420° C.; and
   wherein the alloy is non-ferromagnetic and has a coefficient of thermal expansion between 13.9 to $15.2 \times 10^{-6}$ $K^{-1}$ at 500° C.

2. The cobalt based dental alloy of claim 1, wherein the alloy further comprises up to about 3 wt. % of at least one additive material selected from the group consisting of molybdenum, manganese, aluminum, boron, cerium, gallium, germanium and silicon.

3. The cobalt based dental alloy of claim 2, wherein the alloy comprises from about 5 wt. % to 6 wt. % ruthenium.

4. The cobalt based dental alloy of claim 1, wherein the alloy further comprises less than 5 wt. % of at least one trace additive selected from the group consisting of copper, nickel and iron.

5. The cobalt based dental alloy of claim 1, wherein the sum of Pt and Ru is 25 wt. %.

6. The cobalt based dental alloy of claim 1, wherein the alloy composition comprises 45.0 wt. % cobalt, 29.3 wt. % chromium, 20 wt. % platinum, and 5.7 wt. % ruthenium.

7. The cobalt based dental alloy of claim 1, wherein the alloy has a thermal expansion coefficient of from 14.3 to $14.7 \times 10^{-6}$ $K^{-1}$ at 500° C.

8. The cobalt based dental alloy of claim 1, wherein the alloy has a thermal expansion coefficient of from 14.6 to $15 \times 10^{-6}$ $K^{-1}$ at 600° C.

9. The cobalt based dental alloy of claim 1, wherein the alloy has a Vickers Hardness of from 180 to 332 HV, a tensile strength of at least 900 to 1200 MPa, a Young's modulus of at least 470 to 780 MPa, and an elongation of at least 2% to 14%.

10. A dental product comprising: a body for dental application, said body being formed of a non-magnetic cobalt based dental alloy comprising:
    40 wt. % to 50 wt. % Co;
    19 wt. % to 27 wt. % Pt;
    up to 6 wt. % Ru; and
    23 wt. % to 32 wt. % Cr;
    wherein the Pt comprises or combination of Pt and Ru comprise from 25 wt. % to 33 wt. % of the dental alloy composition;
    wherein the alloy has a liquidus temperature of from 1370 to 1420° C.; and
    wherein the alloy is non-ferromagnetic and has a coefficient of thermal expansion between 13.9 to $15.2 \times 10^{-6}$ $K^{-1}$ at 500° C.

11. The dental product of claim 10, wherein the alloy further comprises up to about 3 wt. % of at least one additive material selected from the group consisting of molybdenum, manganese, aluminum, boron, cerium, gallium, germanium and silicon.

12. The dental product of claim 11, wherein the alloy comprises from 5 to 6 wt. % ruthenium.

13. The dental product of claim 10, wherein the alloy further comprises less than 5 wt. % of at least one trace additive selected from the group consisting of copper, nickel and iron.

14. The dental product of claim 10, where the sum of Pt and Ru is 25 wt. %.

15. The dental product of claim 10, wherein the alloy composition comprises 45.0 wt. % cobalt, 29.3 wt. % chromium, 20 wt. % platinum, and 5.7 wt. % ruthenium.

16. The dental product of claim 10, wherein the alloy has a thermal expansion coefficient of from about 14.3 to $14.7 \times 10^{-6}$ $K^{-1}$ at 500° C.

17. The dental product of claim 10, wherein the alloy has a thermal expansion coefficient of from 14.6 to $15 \times 10^{-6}$ $K^{-1}$ at 600° C.

18. The dental product of claim 10, wherein the alloy has a Vickers Hardness of from 180 to 332 HV, a tensile strength of from 900 to 1200 MPa, a Young's modulus of from 470 to 780 MPa, and an elongation of from 2 to 14%.

* * * * *